United States Patent [19]  
Piesch et al.

[11] 4,360,459  
[45] Nov. 23, 1982

[54] SULPHUR DYESTUFFS OF THE CARBAZOLE SERIES

[75] Inventors: Steffen Piesch, Oberursel; Wolf Weidemüller, Frankfurt am Main, both of Fed. Rep. of Germany

[73] Assignee: Cassella Aktiengesellschaft, Frankfurt, Fed. Rep. of Germany

[21] Appl. No.: 251,172

[22] Filed: Apr. 6, 1981

[30] Foreign Application Priority Data

Apr. 9, 1980 [DE] Fed. Rep. of Germany ....... 3013625

[51] Int. Cl.$^3$ ............................................. C07D 49/12
[52] U.S. Cl. ..................................... 260/130; 348/440
[58] Field of Search ................................ 260/130, 315

[56] References Cited

U.S. PATENT DOCUMENTS 2,212,821 8/1940 Bigelow et al. ..................... 260/130

OTHER PUBLICATIONS

"Die Carbazolgruppe"-Dr. Georg Cohn-p. 98 (1919).

Primary Examiner—Robert W. Ramsuer  
Attorney, Agent, or Firm—Connolly and Hutz

[57] ABSTRACT

Carbazoleazomethines are prepared and sulfur dyestuffs are prepared by sulphurizing a carbazoleazomethine of the formula

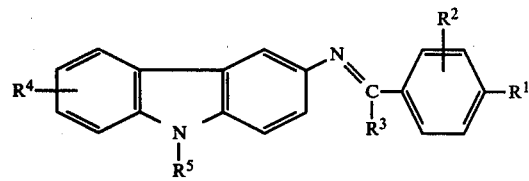

wherein
$R^1$ is hydrogen, hydroxyl, halogen, nitro, alkyl having 1 to 8 carbon atoms, alkoxy having 1 to 8 carbon atoms, dialkylamino having 1 to 4 carbon atoms per alkyl, alkanoyloxy having 1 to 8 carbon atoms, benzoyloxy, alkanoylamino having 1 to 8 carbon atoms or benzoylamino;
$R^2$ is hydrogen, hydroxyl, halogen, alkyl having 1 to 8 carbon atoms or alkoxy having 1 to 8 carbon atoms;
$R^3$ is hydrogen or alkyl having 1 to 7 carbon atoms;
$R^4$ is hydrogen or halogen; and
$R^5$ is hydrogen or alkyl having 1 to 8 carbon atoms.

3 Claims, No Drawings

SULPHUR DYESTUFFS OF THE CARBAZOLE SERIES

The present invention relates to new sulphur dyestuffs which can be prepared, by processes which are in themselves known, by sulphurising carbazoleazomethines of the formula I

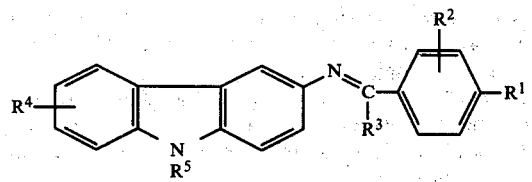

wherein the symbols $R^1$ to $R^5$ have the meanings indicated below, to their use for dyeing cellulose and polyamide and to the new carbazoleazomethines of the formula I which are required for the preparation of the new dyestuffs.

It is known to prepare sulphur dyestuffs by reacting suitable organic compounds with sulphur and optionally alkali metal sulphides or polysulphides at an elevated temperature. A concise survey covering the most important groups of suitable starting materials known at the present time is to be found, for example, in Kirk-Othmer, "Encyclopedia of Chemical Technology", 2nd edition, volume 19, pages 425-435. In keeping with the great industrial importance of sulphur dyestuffs, there is a large number of publications which relate to the general outline of the various sulphurisation processes, such as "bake-melt" and "boil-melt", and are also devoted to individual groups of suitable starting materials and sulphur dyestuffs.

In relation to the present invention, the following monographs in particular appear to be of interest: O. Lange, "Die Schwefelfarbstoffe, ihre Herstellung und Verwendung" ("The Sulphur Dyestuffs, their Manufacture and their Use"), 2nd edition, Spamer, Leipzig (1925) and K. Venkataraman, "The Chemistry of Synthetic Dyes and Pigments", volume 2, Academic Press, Inc., New York, (1952), chapter 35.

German Patent No. 135,335 has disclosed a process for the manufacture of sulphur dyestuffs, in which aromatic methyleneamido compounds, nitro-, amido- and hydroxy-benzylamido compounds and also nitro-, amido- and hydroxy-benzylideneamido compounds, specifically those containing the methylene, benzyl or benzylidene group, respectively, directly linked to nitrogen, are heated with alkali metal sulphides and sulphur or an alkali metal hydroxide solution and sulphur.

Some of the starting materials used in this text constitute azomethines formed from nuclear-substituted benzaldehyde and nuclear-substituted aniline derivatives. Inter alia, this text also describes, as a tabular example, the sulphurisation of 4-(4-nitrobenzylideneamino)-4'-nitrodiphenylamine-3'-sulphonic acid to give a sulphur dyestuff which dyes cotton yellowish-green.

The only dyestuff of this series to gain acceptance in industry is C.I. Sulphur Yellow 8. However, this dyestuff has a light fastness rating of only approx. 3 and thus does not meet practical requirements.

It is known from German Patent No. 165,126 to subject aminonaphthalenesulphonic acid derivatives to a condensation reaction with benzaldehyde or its nitro derivative to give the corresponding azine and then to react the latter under mild conditions with an alkali metal polysulphide. This procedure does not give dyestuffs, but colourless derivatives of naphthothiazole.

It is also already known to sulphurise 3,6-dinitrocarbazole. This gives C.I. Sulphur Brown 6, the properties of which are not recorded by the Color Index because of this dyestuff's complete lack of importance.

It is known from a whole series of patents, for example German Patent No. 218,371, British Pat. No. 2918/09, U.S. Pat. No. 919,572 and the appropriate reprints in "Friedländer", volume 10, pages 256, 258, 71-74 and 75-81, to sulphurise (leuco)-carbazoleindophenols of the formula

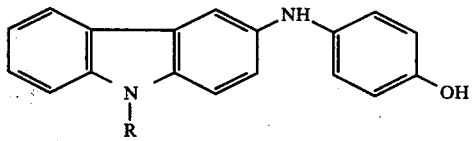

wherein R is hydrogen or ethyl, to give the blue sulphur dyestuffs C.I. Sulphur Blue 42 and 43.

Further derivatives of carbazole have hitherto not been converted into sulphur dyestuffs, although C.I. Sulphur Blue 42 and 43 mentioned above have excellent properties and have been known for 70 years. When it is borne in mind that dyestuffs of this type would also have been of very great interest in other shades than blue, it will be realised that all attempts to extend the field of carbazole sulphur dyestuffs have hitherto come to nothing.

It has now been found that it is possible to enrich the range of sulphur dyestuffs with further very attractive and desirable yellow, olive-green and brown shades and to prepare sulphur dyestuffs having fastness properties which are excellent for this class and very advantageous opportunities for application, if carbazoleazomethines of the formula I

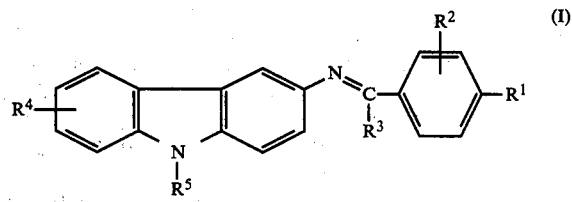

wherein $R^1$ denotes hydrogen, hydroxyl, halogen, nitro, alkyl having 1 to 8 C atoms, alkoxy having 1 to 8 C atoms, dialkylamino having 1 to 4 C atoms per alkyl group, alkanoyloxy having 1 to 8 C atoms, benzoyloxy, alkanoylamino having 1 to 8 C atoms or benzoylamino, $R^2$ denotes hydrogen, hydroxyl, halogen, alkyl having 1 to 8 C atoms or alkoxy having 1 to 8 C atoms, $R^3$ denotes hydrogen or alkyl having 1 to 7 C atoms and $R^4$ denotes hydrogen or halogen and $R^5$ denotes hydrogen or alkyl having 1 to 8 C atoms, are sulphurised by processes which are in themselves known, preferably by the process of "boil-melt".

Alkyl radicals represented by $R^1$, $R^2$, $R^3$ or $R^5$ can be linear or branched and are optionally substituted by a halogen atom, particularly a chlorine atom. Linear, unsubstituted alkyl radicals are preferred.

Particularly advantageous dyestuffs are obtained if carbazoleazines of the formula I in which $R^1$ denotes hydroxyl, chlorine, nitro, alkyl having 1 to 4 C atoms, alkoxy having 1 to 4 C atoms or dialkylamino having 1 or 2 C atoms per alkyl group, $R^2$ denotes hydrogen, hydroxyl, chlorine, alkyl having 1 to 4 C atoms or alkoxy having 1 to 4 C atoms, $R^3$ denotes hydrogen or alkyl having 1 to 3 C atoms and $R^4$ denotes hydrogen and $R^5$ denotes hydrogen or alkyl having 1 to 4 C atoms, are sulphurised. The substituent $R^4$ is preferably in the 6-position or 8-position in the carbazole system.

The compounds of the formula I can also be sulphurised to give sulphur dyestuffs according to the invention if they contain, in the proportions of up to approx. 25%, which are customary in industry, the isomers produced in their production, in which the benzalamino group is attached in the 1-position of the carbazole system.

The compounds I are sulphurised in the boil-melt procedure in the manner which is in itself known, by reaction with sulphur and/or an alkali metal polysulphide in an aqueous medium or an organic solvent at an elevated temperature, as described, for example, in O. Lange, "Die Schwefelfarbstoffe, ihre Herstellung und Verwendung" ("The Sulphur Dyestuffs, their Manufacture and their Use") (1912), pages 208–220 and 223–225, or in Venkataraman, "The Chemistry of Synthetic Dyes", volume 2 (1952), page 1062 et seq. and page 1103 et seq., and also volume 7 (1974), page 24 et seq., Academic Press, New York, San Francisco and London.

Boil-melts which are particularly suitable are those which employ an alkali metal polysulphide, 0.1 to 10 mols, preferably 0.5 to 4 mols, of sodium sulphide and 1 to 30 mols, preferably 2 to 20 mols, of sulphur being employed per mol of the product to be sulphurised. These melts are carried out in the solvents which are customary for sulphurising melts. Suitable solvents in which the reaction can appropriately be carried out are alkanols or cycloalkanols having 1 to 7 C atoms, such as, for example, methanol, ethanol, propanol, isopropanol, n-butanol, isobutanol, amylalcohol, cyclohexanol and methylcyclohexanol, and monoalkyl ethers, particularly monoalkyl ethers of ethylene glycol and diethylene glycol, such as, for example, ethylene glycol monomethyl ether, monoethyl ether and monopropyl ether or diethylene glycol monomethyl ether, monoethyl ether and monopropyl ether.

The sulphurisation of the compounds of the formula I can be effected with the exclusion of water or in a purely aqueous medium, but is normally carried out in aqueous solvents containing 5 to 70% of water. In the case of solvents which are miscible with water, it is preferable to carry out the reaction using the customary hydrotropic compounds, for example the sodium salt of xylenesulphonic acid.

The boil-melt procedure is effected at temperatures of 80° to 300° C., preferably 110° to 250° C. and particularly within the range from 120° to 180° C. and appropriately with a reaction time of 1 to 100, preferably 20 to 80, hours.

If the known disadvantages of the so-called "bake-melt" or "sulphurising melt" procedures are accepted (compare O. Lange, "Die Schwefelfarbstoffe" ("The Sulphur Dyestuffs") (1912), pages 221 and 222), the compounds of the formula I can also be sulphurised by this process to give sulphur dyestuffs.

In the preparation of the sulphur dyestuffs according to the invention by bake-melting, the latter are heated at 200° to 300° C. for 1 to 20 hours with the 7-fold to 30-fold molar quantity of sulphur and the 2-fold to 6-fold molar quantity of sodium sulphide. Here too, it is also possible to carry out the reaction initially in a solvent, preferably in water, in order to ensure that the reaction batch is thoroughly homogeneous. The solvent is then evaporated off and the solvent-free melt is warmed to the desired temperature, appropriately in an atmosphere of a protective gas.

The sulphur dyestuffs prepared by the process according to the invention can be isolated in a customary manner and then made into the various commercial forms. If the sulphurisation has been carried out in a water-miscible solvent in the presence of hydrotropic compounds, the melt can also be processed further directly, without isolating the dyestuff, to give liquid dyestuffs ready for use.

The sulphur dyestuffs which can be prepared in accordance with the invention can be reduced very readily by reducing agents such as are customary for the reduction of a sulphur dyestuff and in this way produce clear, aqueous solutions. They can be employed for dyeing, preferably, vegetable fibres by the known processes which are customary for dyeing by means of sulphur dyestuffs or sulphur vat dyestuffs.

For this purpose they are converted, by means of reducing agents, preferably sodium dithionite, sodium sulphide or sodium hydrogen sulphide, but possibly also by means of sodium formaldehyde-sulphoxylate, glucose or organic mercapto compounds, such as, for example, thioglycerol or thioglycollic acid, into the soluble leuco form, which is absorbed onto the fibres. Dyestuffs which are present in a liquid form ready for use contain the soluble leuco form and a reducing agent and can also be used for dyeing the fibres mentioned without a further addition of reducing agents.

After the dyestuffs have been absorbed onto the fibres, the leuco form of the sulphur dyestuffs according to the invention is re-converted into the insoluble form of the sulphur dyestuff in a customary manner, for example, by "hanging" the dyeings in the air or oxidation with oxidising agents, such as, for example, hydrogen peroxide or an alkali metal dichromate, chlorite or iodate. The sulphur dyestuffs which can be prepared in accordance with the invention dye cellulose in full yellow, gold-brown and olive-green shades and thus constitute an extremely valuable supplement to the carbazole sulphur dyestuffs C.I. Sulphur Blue 42 and 43 which are comparable in coloristic properties.

When applied to cellulose fibres, the dyestuffs according to the invention have the following advantages, in particular: very good fastness to light, very good fastness to wet processing, very good fastness, as specified in DIN 54,015, to peroxide washing and very good fastness to mercerising.

A further advantage of the dyestuffs according to the invention is their stability to the action of alkali metal dithionites and alkali metal formaldehyde-sulphoxylates and also the fact that they can be manufactured easily on an industrial scale.

Polyamide can also be dyed by means of the sulphur dyestuffs according to the invention. Depending on the reducing agent and the quantity of dyestuff employed, yellow to green-black colour shades are obtained.

Hitherto, the only known representative of the carbazoleazomethines of the formula I required for the preparation of the sulphur dyestuffs according to the invention is the compound of the formula

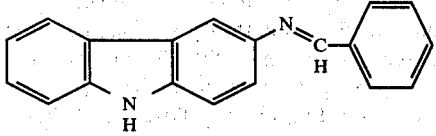

(Cohn, "Die Carbazolgruppe" ("The Carbazole Group"), page 98).

The carbazoleazomethines of the formula I are obtained by subjecting derivatives of aminocarbazole of the formula II

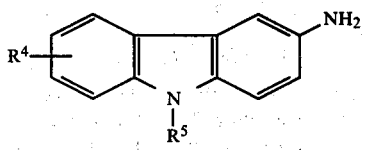

wherein $R_4$ and $R^5$ have the abovementioned meaning, or technical mixtures of isomers thereof, to a condensation reaction, with the elimination of water, with aldehydes or ketones of the formula III

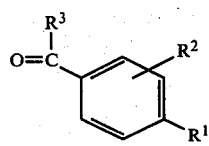

wherein $R^1$, $R^2$ and $R^3$ have the abovementioned meanings.

Technical mixtures of isomers of the 3-aminocarbazoles of the formula II are to be understood as meaning products containing all the isomeric aminocarbazoles which are formed in the manufacture of the 3-aminocarbazoles on an industrial scale. Besides the main product, the 3-aminocarbazoles, crude technical products of this type contain for the most part the corresponding 1-aminocarbazoles.

Accordingly, the carbazoleazomethines, according to the invention, of the formula I which are obtained using technical, crude 3-aminocarbazoles as the starting material, also contain, as a rule, proportions of the isomeric compounds in which the benzalamino group is present in the 1-position of the carbazole skeleton.

The reaction conditions of this condensation reaction are known from a large number of publications on the formation of azomethines from amines and carbonyl compounds. (Compare Chem. Rev. 26 (1940), pages 297–338; Houben-Weyl, "Methoden der organischen Chemie" ("Methods of Organic Chemistry"), volume 7/1, pages 456 and 457; S. Patai, "The Chemistry of the Amino Group" (1968) Interscience Publishers, page 352; and A. E. A. Werner, Journ. Chem. Soc. London 23 (1944), page 214).

In general, the condensation reaction is carried out by heating the components at temperatures from 50° to 200° C., either in the absence of a solvent or in an organic solvent, until the elimination of water is complete. If the reaction is carried out without using a solvent, it is appropriate to carry out the reaction at temperatures above 90° C., particularly above 100° C., in order to achieve removal of the water of reaction from the reaction system as rapidly as possible. In any case the temperature selected should be sufficiently high for a homogeneous melt to be present.

If the condensation reaction is carried out in an organic solvent, it is appropriate to carry out the reaction at the boiling point of the mixture. In this case the condensation reaction can be promoted if the water split off is removed continuously by distillation.

Examples of suitable solvents for carrying out the condensation reaction are alkanols having 1 to 5, preferably 3 to 4, C atoms, glycol monoalkyl ethers, diglycol monoalkyl ethers, triglycol monoalkyl ethers, cyclic ethers, such as dioxane or tetrahydrofuran, or benzene derivatives, such as toluene, xylene, monochlorobenzene or dichlorobenzene.

In order to accelerate the condensation reaction, the reaction is as a rule carried out in the presence of catalytic quantities (0.1 to 5%) of an inorganic acid (for example hydrochloric acid) or an organic acid (for example formic acid, acetic acid, toluenesulphonic acid, trifluoromethanesulphonic acid or methanesulphonic acid). However, it is also possible (A. Albert et al. Journ. of the Chemical Society, London (1943), page 458) to accelerate the condensation reaction by adding a base.

It is also possible to carry out the reaction entirely in a lower alkanecarboxylic acid as the solvent, for example in acetic acid, propionic acid or butyric acid.

The compounds of the general formulae II and III are known products, in some cases products manufactured on a large industrial scale. If they are not commercially available, they can readily be prepared by simple, known processes.

The following are examples of aminocarbazoles of the formula II: 3-aminocarbazole, 3-amino-6-chlorocarbazole, 3-amino-8-chlorocarbazole and a technical mixture of 1-aminocarbazole and 3-aminocarbazole.

The following are examples of aldehydes or ketones of the formula III: p-hydroxybenzaldehyde; o-hydroxybenaldehyde; 3,4-dihydroxybenzaldehyde; vanillin; p-nitrobenzaldehyde, o-, m- or p-methylbenzaldehyde, o-, m- or p-chlorobenzaldehyde, 2,4-dichlorobenzaldehyde, p-acetylaminobenzaldehyde, p-hydroxyacetophenone, p-hydroxypropiophenone, resacetophenone or p-dimethylaminobenzaldehyde; p-hydroxyisocaprylophenone or 2,4-dihydroxybutyrophenone.

The following illustrative embodiments illustrate the preparation and use of the sulphur dyestuffs according to the invention and the preparation of the intermediate products, according to the invention, of the general formula I.

EXAMPLE 1

(a) A mixture of 200 ml of diethylene glycol monoethyl ether, 90 g of sulphur, 71 g of concentrated (60% strength) sodium sulphide, 50 g of sodium xylenesulphonate and 50 g of a carbazoleazomethine of the formula

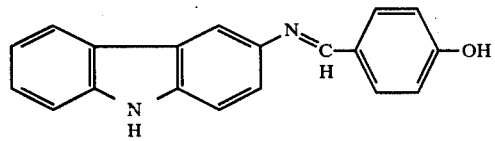

is warmed to 135° C. and is stirred at this temperature for 42 hours under a reflux condenser. The hot melt is then stirred into a 2 l of water warmed to 60° C., 100 g of sodium bisulphite are added to the resulting suspension and the mixture is subsequently stirred for 2 hours at 70°–80° C. The dyestuff is then filtered off, washed with water until it is virtually neutral and dried. The yield of dyestuff is 68 g. From a dithionite vat, the dyestuff dyes cotton a full yellow shade which has very good fastness to wet processing and light. If the sulphurisation is carried out, not at 135° C., but at 170° C., the procedure being in other respects as specified in the above example, a dyestuff is obtained which dyes cotton from a dithionite vat in a fine, clear, golden-brown shade. The fastness properties of this dyeing are also very good.

(b) The carbazoleazomethine employed for the preparation of the above sulphur dyestuff, 3-(4-hydroxybenzalamino)-carbazole, can be prepared as follows 300 g of 3-aminocarbazole, 205 g of 4-hydroxybenzaldehyde and 5 g of p-toluenesulphonic acid are introduced into 1.5 l of isopropanol, while stirring, and the mixture is heated to approx. 85° C. and boiled under reflux for 18 hours. An additional 20 g of p-hydroxybenzaldehyde are then added and the mixture is boiled under reflux for a further 5 hours. The resulting reaction mixture is then cooled to 0° C. and left to crystallise and the crystals are filtered off cold and washed with approx. 100 ml of cold isopropanol. This gives 336 g (~70% of theory) of pale yellow crystals, melting point 249°–251° C.

A sulphur dyestuff according to the invention which dyes in a clear yellow-brown shade is obtained by sulphurising, in accordance with Example 1a, an azomethine which has been obtained as follows 300 g of crude 3-aminocarbazole, 205 g of 4-hydroxybenzaldehyde and 5 g of p-toluenesulphonic acid are introduced into 1.5 l of xylene, while stirring, and the mixture is heated to 140° C. under a water separator. The mixture is stirred at this temperature for 18 hours, 26 ml of water being collected in the water separator while the mixture is boiled under reflux. A further 20 g of p-hydroxybenzaldehyde and 1 l of xylene are then added and the mixture is stirred for a further 5 hours under the water separator, a further 3 ml of water being removed.

The xylene is then largely distilled off and the residue is triturated with a little toluene and filtered and the filter residue is washed twice with a little toluene. The crude yield is 480 g (~100% of theory). In the crude state, the substance melts at 228° C. and it can be sulphurised in accordance with section (a) of this example without further purification.

EXAMPLE 2

(a) A mixture of 200 ml of diethylene glycol monoethyl ether, 90 g of sulphur, 71 g of concentrated (60% strength) sodium sulphide, 50 g of sodium xylenesulphonate and 50 g of the carbazoleazomethine of the formula

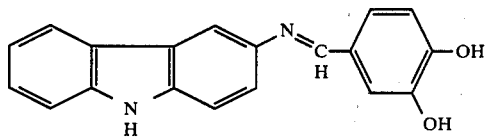

is warmed to 140° C. and is stirred under a reflux condenser for 48 hours at this temperature. The reaction mixture is then cooled to 90° C. and diluted with 400 ml of water, and sulphur dioxide is passed in until the pH value has fallen to 2.5. Stirring is continued for a further 15 minutes at 65° C. and the dyestuff is then filtered off, washed with water until virtually neutral and dried. The yield is 68 g. From a dithionite vat, the dyestuff dyes cotton in a full, clear, yellow-green shade which has very good fastness properties, in particular very good fastness to washing and good fastness to light.

(b) The carbazoleazomethine employed as the starting material in section (a), 3-(3,4-dihydroxybenzalamino)-carbazole, can be prepared analogously to the instructions in Example 1(b), the 205+20 g of 4-hydroxybenzaldehyde employed there being replaced by 232+22.6 g of 3,4-dihydroxybenzaldehyde.

EXAMPLE 3

(a) A mixture of 200 ml of diethylene glycol monoethyl ether, 108 g of sulphur, 71 g of concentrated (60% strength) sodium sulphide, 50 g of sodium xylenesulphonate and 50 g of the carbazoleazomethine of the formula

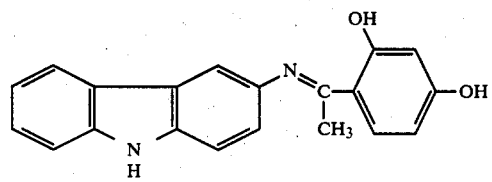

is warmed to 135° C. while stirring and kept at this temperature for 42 hours under a reflux condenser. The reaction mixture is then diluted to a volume of 1 l by adding water and the pH is adjusted to a value of 2.3 by passing in SO$_2$. The pH is then buffered to a value of 4.8 by adding 38° Bé sodium hydroxide solution and the resulting dyestuff is filtered off, washed on the filter until it is neutral and dried. The yield of dyestuff is 172 g. From a dithionite vat, the dyestuff dyes cotton in a full, clear, olive-green shade. The dyeing has very good fastness to wet processing and light.

(b) The carbazoleazomethine employed for the preparation of the above sulphur dyestuff can be prepared as follows 180 g of crude 3-aminocarbazole, 152 g of resacetophenone and 5 g of p-toluenesulphonic acid are introduced into 1.5 l of xylene, while stirring, and the mixture is heated to 140° C. under a water separator. The mixture is stirred at this temperature, while boiling under reflux, until 18 ml of water have been removed in the water separator. The xylene is then largely distilled off, the residue is triturated with a little toluene and filtered and the filter residue is washed twice with a little toluene. The crude yield is 283 g (~90% of theory). In the crude state the substance melts at 250°–265° C. and it can be sulphurised as specified in section (a) of this example without further purification.

EXAMPLE 4

(a) A mixture of 100 ml of diethylene glycol monoethyl ether, 35 g of sulphur, 24 g of concentrated (60% strength) sodium sulphide, 20 g of sodium xylenesulphonate and 25 g of the carbazoleazomethine of the formula

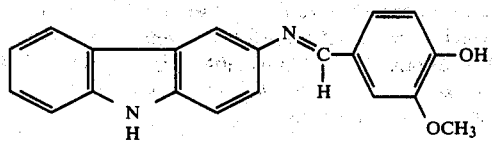

is warmed to 140° C. and stirred under a reflux condenser for 69 hours at this temperature. The hot melt is then stirred into 1 l of water warmed to 60° C. and 50 g of sodium bisulphite are added to the resulting suspension and the mixture is stirred for a further 2 hours at 80° C. The dyestuff is then filtered off, washed with water until it is virtually neutral and dried. The yield of dyestuff is 24 g. From a dithionite vat, the dyestuff dyes cotton a full, greenish-tinged brown shade which has very good fastness to wet processing and light.

(b) The carbazoleazomethine employed for the preparation of the above sulphur dyestuff, 3-(4-hydroxy-3-methoxybenzalamino)carbazole, can be prepared as follows 300 g of 3-aminocarbazole, 255 g of vanillin and 5 g of p-toluenesulphonic acid are introduced into 1.5 l of xylene, while stirring, and the mixture is heated to 140° C. under a water separator. The mixture is stirred for 18 hours at this temperature, 25 ml of water being collected in the water separator while the mixture is boiled under reflux. A further 20 g of vanillin and 1 l of xylene are added and the mixture is stirred for a further 5 hours under the water separator, a further 3 ml of water being removed. The xylene is then largely distilled off, the residue is triturated with a little toluene and filtered and the filtered residue is washed twice with a little toluene. The crude yield is 490 g (~94% of theory). In the crude state the substance melts at 180° to 210° C. and it can be sulphurised as specified in section (a) of this example without further purification.

EXAMPLE 5

(a) A mixture of 200 ml of diethylene glycol monoethyl ether, 90 g of sulphur, 71 g of concentrated (60% strength) sodium sulphide, 50 g of sodium xylenesulphonate and 50 g of the carbazoleazomethine of the formula

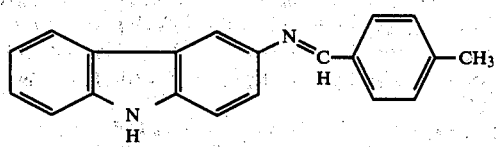

is warmed to 135° C. and stirred under a reflux condenser for 70 hours at this temperature. The reaction mixture is then cooled to 90° C. and diluted to a volume of 1 l with water, and sulphur dioxide is passed in until the pH value has fallen to 3.0. Stirring is continued for a further 15 minutes at 65° C. and the dyestuff is then filtered off, washed with water until it is virtually neutral and dried. The yield is 53 g. From a dithionite vat, the dyestuff dyes cotton in a full, clear, slightly reddish-tinged brown shade which has very good fastness properties, particularly very good fastness to washing and good fastness to light.

(b) The carbazoleazomethine employed as the starting material in section (a), 3-(4-methylbenzalamino)-carbazole, can be prepared analogously to the instructions in Example 4(b), the 255+20 g of vanillin employed there being replaced by 201+16 g of 4-methylbenzaldehyde.

EXAMPLE 6

(a) A mixture of 200 ml of diethylene glycol monoethyl ether, 90 g of sulphur, 71 g of concentrated (60% strength) sodium sulphide, 50 g of sodium xylenesulphonate and 50 g of the carbazoleazomethine of the formula

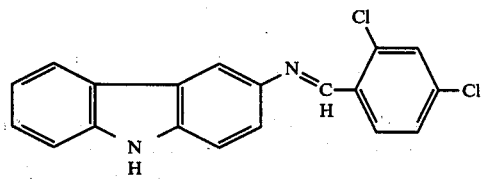

is warmed to 135° C. and stirred under a reflux condenser for 48 hours at this temperature. The hot melt is then stirred into 2 l of water warmed to 60° C., 100 g of sodium bisulphite are added to the resulting suspension and the mixture is stirred for a further 2 hours at 70°–80° C. The dyestuff is then filtered off, washed with water until it is virtually neutral and dried. The yield of dyestuff is 68 g. From a dithionite vat, the dyestuff dyes cotton a full golden-yellow shade which has very good fastness to wet processing and light.

(b) The carbazoleazomethine employed for the preparation of the above sulphur dyestuff, 3-(2,4-dichlorobenzalamino)-carbazole, can be prepared as follows 450 ml of isopropanol, 135 g of crude 3-aminocarbazole, 134 g of 2,4-dichlorobenzaldehyde and 5 ml of concentrated formic acid are boiled under reflux for 8 hours, while stirring. After cooling, the suspension is filtered and the filter residue is washed with approx. 100 ml of isopropanol and dried. This gives 120 g (~50% of theory) of product which has a melting point of approx. 250° C. and is sufficiently pure for sulphurisation. Further quantities of the substance can also be isolated from the mother liquor.

The same carbazoleazomethine is obtained by the following process 300 g of crude 3-aminocarbazole, 294 g of 2,4-dichlorobenzaldehyde and 5 g of p-toluenesulphonic acid are introduced into 1.5 l of xylene, while stirring, and the mixture is heated to 140° C. under a water separator. The mixture is stirred for 18 hours at this temperature, 28 ml of water being collected in the water separator while the mixture is boiled under reflux. The xylene is then largely distilled off, the residue is triturated with a little toluene and filtered and the filter residue is washed twice with a little toluene. The crude yield is 510 g (~91% of theory) of material which, in the crude state, has a melting point (not sharp) of 225° C. and can be sulphurised as specified in section (a) of this example without further purification.

EXAMPLE 7

(a) 50 g of the carbazoleazomethine of the formula

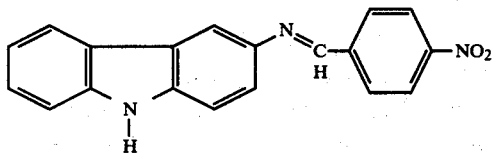

are introduced into a mixture of 50 g of 31% strength aqueous sodium hydrogen sulphide solution, 20 g of sodium xylenesulphonate and 200 g of diethylene glycol monoethyl ether at 25°–26° C., while stirring. In the course of a few minutes the temperature of the mixture rises to 76° C. of its own accord. Stirring is continued for 1 hour at this temperature and 108 g of sulphur and 42 g of concentrated (60% strength) sodium sulphide are then added. The mixture is then warmed to 140° C., while stirring, and is stirred under reflux for a further 60 hours at this temperature. The hot melt is then stirred into 2 l of water warmed to 60° C., 100 g of sodium bisulphite are added to the resulting suspension and the mixture is stirred for a further 2 hours at 80° C. The dyestuff is then filtered off, washed with water until it is virtually neutral and dried. The yield of dyestuff is 77 g. From a dithionite vat, the dyestuff dyes cotton a full, clear, yellowish-tinged brown shade which has very good fastness to wet processing and light.

If the same quantity of the 9-ethyl derivative of the formula

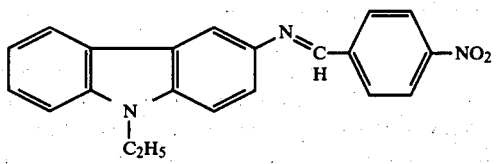

is employed, analogously to the above instructions, instead of 50 g of the above carbazoleazomethine, and if the sulphurisation is carried out at 160° C., 62 g of a sulphur dyestuff which dyes cotton a neutral, clear brown shade are obtained.

(b) The carbazoleazomethine required for the preparation of the above sulphur dyestuff, 3-(4-nitrobenzalamino)-carbazole, is prepared as follows A mixture of 1.5 l of ethylene glycol monoethyl ether, 300 g of 3-aminocarbazole, 250 g of p-nitrobenzaldehyde and 15 ml of formic acid is boiled under reflux for 4 hours, while stirring. The solvent is then driven off on a rotary evaporator, the residue is boiled up with 1 l of methanol and the suspension is filtered. The filter residue is rinsed with approx. 100 ml of methanol and is dried. Red crystals with a melting point of 198°–200° C.; yield 360 g (~70% of theory).

The 9-ethyl derivative is obtained if 346 g of 3-amino-9-ethylcarbazole are reacted with p-nitrobenzaldehyde in accordance with the above instructions, intead of the 300 g of 3-aminocarbazole. The yield is 85% of theory.

Valuable sulphur dyestuffs according to the invention are also obtained if the following carbazoleazomethines are prepared and sulphurised analogously to the above illustrative embodiments.

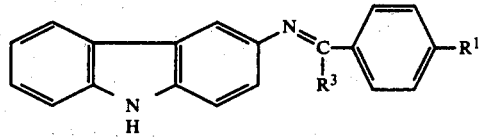

| | |
|---|---|
| $R^1 = $ —COOCH$_3$ | $R^3 = $ H |
| $R^1 = $ —OH | $R^3 = $ —C$_3$H$_7$ |
| $R^1 = $ —OH | $R^3 = $ —C$_8$H$_{17}$(iso) |
| $R^1 = $ —N(CH$_3$)$_2$ | $R^3 = $ H |

What is claimed is:
1. Sulphur dyestuffs prepared by sulphurizing a carbazole derivative according to the boil-melt or bake-melt sulphurization process wherein said carbazole derivative is a carbazoleazomethine of the formula

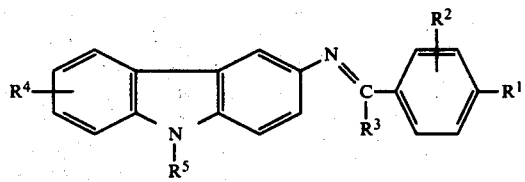

wherein
$R^1$ is hydrogen, hydroxyl, halogen, nitro, alkyl having 1 to 8 carbon atoms, alkoxy having 1 to 8 carbon atoms, dialkylamino having 1 to 4 carbon atoms per alkyl, alkanoyloxy having 1 to 8 carbon atoms, benzoyloxy, alkanoylamino having 1 to 8 carbon atoms or benzoylamino;
$R^2$ is hydrogen, hydroxyl, halogen, alkyl having 1 to 8 carbon atoms or alkoxy having 1 to 8 carbon atoms;
$R^3$ is hydrogen or alkyl having 1 to 7 carbon atoms;
$R^4$ is hydrogen or halogen; and
$R^5$ is hydrogen or alkyl having 1 to 8 carbon atoms.
2. Sulphur dyestuffs according to claim 1 wherein
$R^1$ is hydroxyl, chloro, nitro, alkyl having 1 to 4 carbon atoms, alkoxy having 1 to 4 carbon atoms or dialkylamino having 1 or 2 carbon atoms per alkyl,
$R^2$ is hydrogen, hydroxyl, chloro, alkyl having 1 to 4 carbon atoms or alkoxy having 1 to 4 carbon atoms;
$R^3$ is hydrogen or alkyl having 1 to 3 carbon atoms;
$R^4$ is hydrogen; and
$R^5$ is hydrogen or alkyl having 1 to 4 carbon atoms.
3. Sulphur dyestuffs according to claim 1 or claim 2 prepared by sulphurizing the carbazoleazomethine in accordance with the boil-melt process.

* * * * *